United States Patent
Head et al.

(10) Patent No.: US 9,889,248 B2
(45) Date of Patent: Feb. 13, 2018

(54) SYRINGE STORAGE TRAY

(71) Applicants: BAXALTA GMBH, Zug (CH); BAXALTA INCORPORATED, Bannockburn, IL (US)

(72) Inventors: Brian R. Head, Salem, WI (US); Amy R. Cohen, Grayslake, IL (US); Georgios A. Bertos, Chicago, IL (US); Michael P. Wehrli, Cary, IL (US); Atif M. Yardimci, Lake Forest, IL (US); David V. Alizo, Forest Park, IL (US); Joseph S. Moore, Gurnee, IL (US); Mark E. Williamson, Wonder Lake, IL (US)

(73) Assignees: Baxalta GmbH, Zug (CH); Baxalta Incorporated, Bannockburn, IL (US)

( * ) Notice: Subject to any disclaimer, the term of this patent is extended or adjusted under 35 U.S.C. 154(b) by 0 days.

(21) Appl. No.: 14/400,429

(22) PCT Filed: Dec. 20, 2012

(86) PCT No.: PCT/US2012/070804
§ 371 (c)(1),
(2) Date: Nov. 11, 2014

(87) PCT Pub. No.: WO2013/176703
PCT Pub. Date: Nov. 28, 2013

(65) Prior Publication Data
US 2015/0129442 A1 May 14, 2015

Related U.S. Application Data

(60) Provisional application No. 61/649,586, filed on May 21, 2012.

(51) Int. Cl.
*A61M 5/00* (2006.01)
*B01F 11/00* (2006.01)
(Continued)

(52) U.S. Cl.
CPC ........ *A61M 5/002* (2013.01); *A61M 5/31501* (2013.01); *B01F 11/0005* (2013.01); *A61M 5/008* (2013.01); *A61M 2005/3104* (2013.01)

(58) Field of Classification Search
CPC ....... B65D 1/36; A61M 5/002; A61M 5/3205; A61M 5/31501; A61M 5/008; B61B 19/026
(Continued)

(56) References Cited

U.S. PATENT DOCUMENTS 2,856,925 A * 10/1958 Helmer ............. A61M 5/31591
604/210
2,955,705 A * 10/1960 Krueger, Sr. ........ A61B 19/026
206/365
(Continued)

FOREIGN PATENT DOCUMENTS

EP 1595561 A2 11/2005
EP 1930040 A1 6/2008
(Continued)

OTHER PUBLICATIONS

International Preliminary Report on Patentability, International Application No. PCT/US2012/070804, dated Nov. 25, 2014.
(Continued)

*Primary Examiner* — Steven A. Reynolds
(74) *Attorney, Agent, or Firm* — Troutman Sanders LLP (57) ABSTRACT

A storage tray for one or more syringes includes a recess for each of the syringes to be held in the tray. Each recess has first and second opposed sidewalls that define a space therebetween for receiving the barrel of the syringe. Each of the first and second sidewalls has one or more deformable projections thereon that protrude into the space between the sidewalls for positively retaining the barrel of the syringe between the first and second sidewalls. Additionally, a slot (Continued)

is provided for receiving the thumb rest of the plunger. The slot includes a third sidewall oriented generally transverse to the first and second sidewalls, with the third sidewall including a further projection for engaging a surface of the thumb rest. Preferably, a plurality of such transverse slots is provided to accommodate different positions of the plunger relative to the syringe barrel. The tray also includes a relieved portion intermediate the first and second sidewalls and the slot that provides access to a proximal portion of the syringe barrel to facilitate removal of the syringe from the tray.

21 Claims, 8 Drawing Sheets (51) Int. Cl.
*A61M 5/315* (2006.01)
*A61M 5/31* (2006.01)

(58) Field of Classification Search
USPC .............................. 206/366, 365, 364, 564
See application file for complete search history.

(56) References Cited

U.S. PATENT DOCUMENTS

| | | | | |
|---|---|---|---|---|
| 3,372,798 | A | 3/1968 | Thomas | |
| 3,770,026 | A * | 11/1973 | Isenberg | A61M 5/31525 141/2 |
| 3,820,652 | A | 6/1974 | Thackston | |
| 3,937,219 | A * | 2/1976 | Karakashian | A61M 5/002 206/365 |
| 4,073,321 | A * | 2/1978 | Moskowitz | A61M 5/1782 141/27 |
| 4,246,898 | A * | 1/1981 | Travalent | A61M 5/31551 604/210 |
| 4,563,178 | A * | 1/1986 | Santeramo | A61M 5/1782 141/27 |
| 4,589,870 | A | 5/1986 | Citrin | |
| 4,657,138 | A * | 4/1987 | Watson | 206/366 |
| 4,671,408 | A * | 6/1987 | Raines et al. | 206/365 |
| 4,753,345 | A * | 6/1988 | Goodsir et al. | 206/366 |
| 4,767,008 | A * | 8/1988 | Warnecke et al. | 206/570 |
| 4,863,451 | A * | 9/1989 | Marder | 604/403 |
| 4,921,487 | A | 5/1990 | Buffet | |
| 4,979,616 | A * | 12/1990 | Clanton | A61M 5/3205 206/364 |
| 5,007,535 | A * | 4/1991 | Meseke | A61B 19/0256 206/363 |
| 5,078,267 | A * | 1/1992 | Wright | A61M 5/002 206/364 |
| 5,133,454 | A * | 7/1992 | Hammer | 206/364 |
| 5,156,267 | A * | 10/1992 | Yates et al. | 206/364 |
| 5,293,993 | A * | 3/1994 | Yates et al. | 206/365 |
| 5,385,558 | A * | 1/1995 | Cottone, Sr. | A61M 5/31555 604/208 |
| 5,385,559 | A | 1/1995 | Mannix | |
| 5,772,031 | A * | 6/1998 | Landis | A61B 19/026 206/363 |
| 5,811,061 | A * | 9/1998 | Martinson | B01D 17/0217 422/559 |
| D430,015 | S * | 8/2000 | Himbert | D24/227 |
| 6,216,885 | B1 * | 4/2001 | Guillaume | A61M 5/008 206/366 |
| 6,228,324 | B1 * | 5/2001 | Hasegawa et al. | 422/30 |
| 6,585,696 | B2 | 7/2003 | Petersen et al. | |
| 6,595,362 | B2 * | 7/2003 | Penney et al. | 206/364 |
| 7,018,089 | B2 * | 3/2006 | Wenz | A61M 5/31511 206/219 |
| 7,048,120 | B2 * | 5/2006 | Pond | 206/366 |
| 7,476,218 | B2 * | 1/2009 | Bloom | A61M 5/31501 604/110 |
| 7,597,196 | B2 * | 10/2009 | Langone | A61M 5/002 206/364 |
| 7,901,383 | B2 * | 3/2011 | Follman | A61B 5/1411 206/571 |
| 8,216,192 | B2 | 7/2012 | Burroughs | |
| 8,672,881 | B2 * | 3/2014 | Nagamatsu | 604/97.02 |
| 8,974,424 | B2 * | 3/2015 | Soma | A61M 5/315 604/187 |
| 2002/0108875 | A1 * | 8/2002 | Feinberg et al. | 206/364 |
| 2002/0185406 | A1 * | 12/2002 | Massengale | A61B 19/026 206/571 |
| 2008/0125722 | A1 | 5/2008 | Hess et al. | |
| 2008/0221515 | A1 * | 9/2008 | Nagamatsu | A61M 25/1018 604/97.02 |
| 2009/0093757 | A1 | 4/2009 | Tennican | |
| 2009/0227958 | A1 | 9/2009 | Burroughs | |
| 2009/0326479 | A1 | 12/2009 | Janish | |
| 2010/0012537 | A1 * | 1/2010 | Farrar et al. | 206/364 |
| 2010/0181218 | A1 * | 7/2010 | Beccaro et al. | 206/365 |
| 2013/0245492 | A1 | 9/2013 | Klenk | |
| 2014/0166514 | A1 * | 6/2014 | Martin et al. | 206/365 |
| 2014/0224688 | A1 * | 8/2014 | Slemmen et al. | 206/365 |
| 2014/0352724 | A1 | 12/2014 | Meyer | |
| 2015/0129442 | A1 | 5/2015 | Head | |

FOREIGN PATENT DOCUMENTS

| | | |
|---|---|---|
| JP | 8207960 | 8/1996 |
| JP | 2001104475 A | 4/2001 |
| JP | 2007290720 A | 11/2007 |
| JP | 2008067989 A | 3/2008 |
| JP | 2011006154 A | 1/2011 |
| WO | WO-2007/130809 A2 | 11/2007 |

OTHER PUBLICATIONS

International Search Report and Written Opinion, international application No. PCT/US2012/070804, dated Jun. 4, 2013.

\* cited by examiner

SYRINGE STORAGE TRAY

CROSS-REFERENCE TO RELATED APPLICATIONS

This is the U.S. national phase of International Patent Application No. PCT/US2012/070804, which has an international filing date of Dec. 20, 2012, and claims the priority benefit of U.S. Provisional Application No. 61/649,586, filed May 21, 2012. The entire contents of each of the foregoing is incorporated by reference herein.

FIELD OF THE DISCLOSURE

This disclosure relates to a storage and handling system for one or more syringes and, more particularly, a storage tray for one or more prefilled syringes.

BACKGROUND

Prefilled syringes are increasingly being used as an alternative to vial-based systems. Prefilled syringes have the potential to both minimize the potential of microbial contamination and reduce medication dosing errors, while also providing enhanced convenience and ease of use. Further, the use of prefilled syringes is likely to reduce the amount of overfill when compared to single-dose vials, leading to the optimization of the number of doses that may be obtained from a given volume of the substance to be administered. These advantages of prefilled syringes are especially valuable when the substances to be administered are of a high cost and/or prepared in small quantities, such as gene-based and cellular biologic medical products which may be created from the patient's own stem cells.

Once prefilled, a safe and effective system for handling and delivery of the prefilled syringes to the patient is required. In particular, the relative position of the plunger to the barrel of the syringe must be substantially fixed during shipment to help insure the sterility of the syringe and its contents. When the substances contained in the syringes are high value product, such as biologics, this becomes even more important. Pursuant to the present disclosure a handling and delivery system is provided that includes an improved tray for storage and shipment of one or more prefilled syringes.

SUMMARY OF THE DISCLOSURE

By way of the present disclosure, a storage tray for one or more syringes is provided, each syringe comprising a plunger with a thumb rest and a barrel. In accordance with one aspect of the disclosure, the storage tray includes a first means for removably securing the barrel of the syringe to the tray and second means for maintaining a predetermined position of the plunger relative to the barrel. One or both of the first means and the second means may be formed integrally with the tray. Further, one or both of the first means and the second means may comprise a biasing member. The second means preferably engages the thumb rest of the plunger or, alternatively may engage the shaft of the plunger. The first means may engage the sidewall of the barrel, or alternatively or additionally engage the tip of the barrel.

In accordance with one aspect of the disclosure, the storage tray preferably comprises a recess for each of the syringes to be held in the tray, with each recess further preferably comprising a first segment configured to hold the barrel of the syringe, a second segment for holding the plunger in a pre-determined axial relation to the barrel, and a third segment intermediate the first and second segments configured to provide access to a portion of the barrel sufficient to permit gripping of the barrel by the fingers of a user.

More particularly, each recess preferably has first and second opposed sidewalls that define a space therebetween for receiving the barrel of the syringe. Each of the first and second sidewalls preferably has one or more deformable projections thereon that protrude into the space between the sidewalls for positively retaining the barrel of the syringe between the first and second sidewalls. Additionally, a transverse slot is preferably provided for receiving the thumb rest of the plunger, with the slot comprising a third sidewall oriented generally perpendicularly to the first and second sidewalls, with the third sidewall including a further projection for engaging a surface of the thumb rest. More preferably, the second segment of each recess comprises a plurality of slots configured to receive the thumb rest of the plunger at a plurality of different positions of the plunger relative to the syringe barrel.

In accordance with another aspect, the tray also preferably includes a relieved portion that provides access to a proximal portion of the syringe barrel to facilitate removal of the syringe from the tray.

In another aspect of the disclosure, the tray includes a plurality of corners, and the corners are rounded. Further, the tray may comprise an outer edge in the form of a flange.

In a further aspect, each recess may be provided with third and fourth opposed sidewalls between which is received a length of the plunger disposed between the thumb rest and the proximal end of the barrel.

BRIEF DESCRIPTION OF THE DRAWINGS

These and other aspects of the present subject matter are described in the following detailed description and shown in the attached figures, of which.

DETAILED DESCRIPTION

A more detailed description of a syringe storage tray in accordance with the present disclosure is set forth below. It should be understood that the description below of various specific embodiments is intended to be exemplary, and not exhaustive of all possible variations. Thus, the scope of the disclosure is not intended to be limiting, and should be understood to encompass further variations or embodiments that would occur to persons of ordinary skill.

Turning to the drawings, there is seen a syringe storage tray, generally designated 10, in accordance with the present disclosure. The tray 10 may be thermoformed from a plastic material, such as, for example, PETE (polyethylene therephthalate) or PETG (polyethylene therephthalate glycol), or any other material which provides the tray with the desired structural integrity, is readily susceptible to sterilization, and is easily disposed of or recycled.

Figure 1:
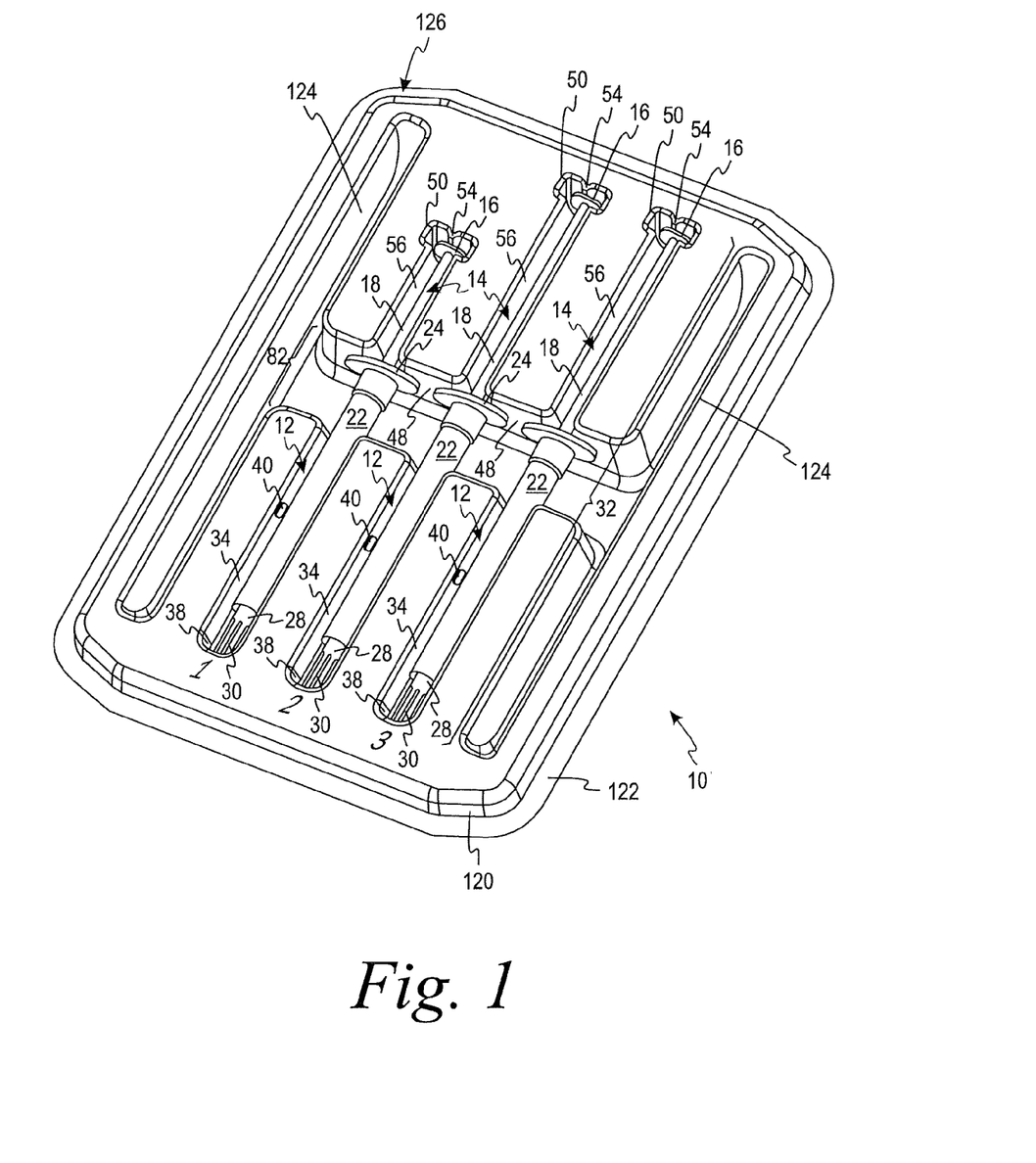
FIG. 1 is a perspective view of a syringe storage tray according to the present disclosure in combination with three prefilled syringes.
Figure 2:
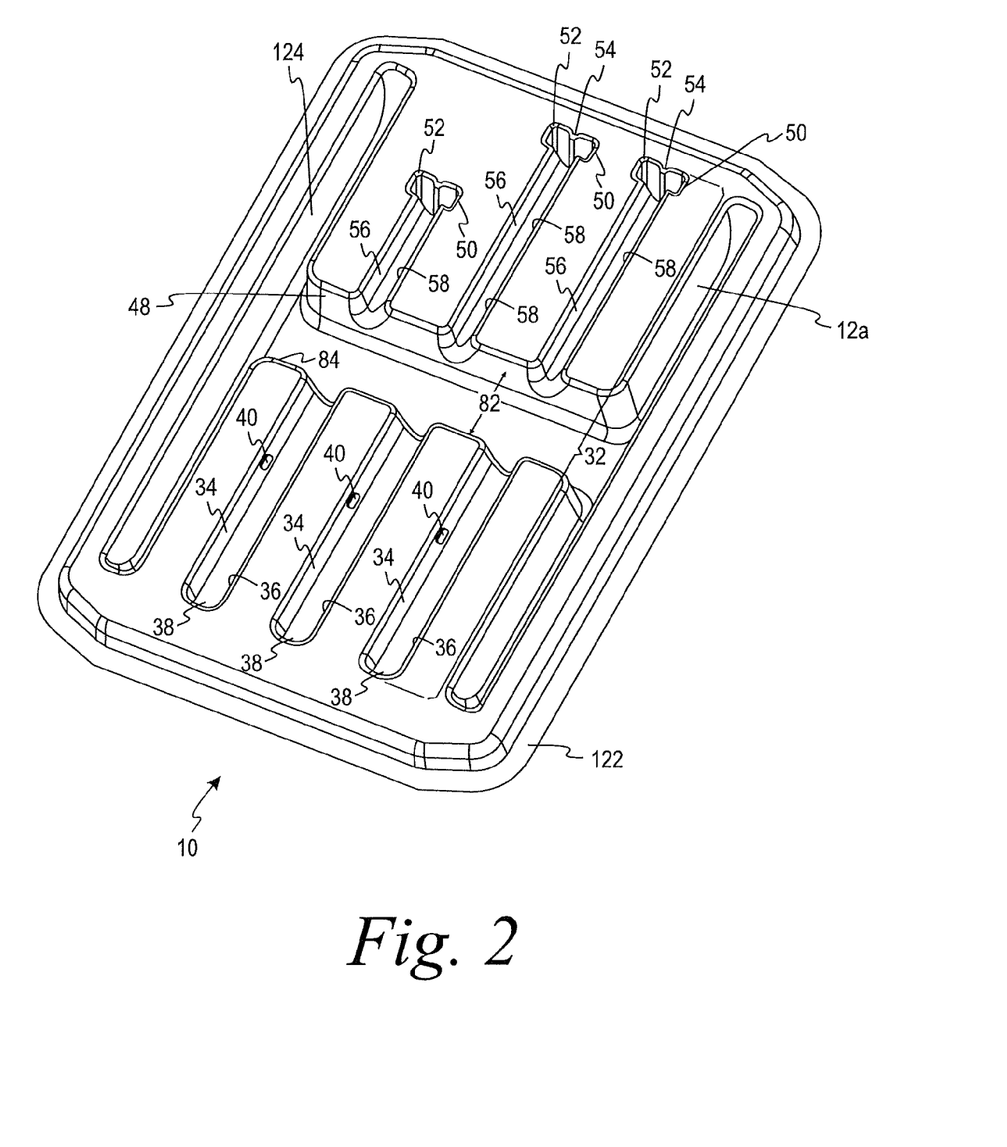
FIG. 2 is a perspective view of a syringe storage tray similar to FIG. 1, except that the prefilled syringes have been removed.
Figure 3:
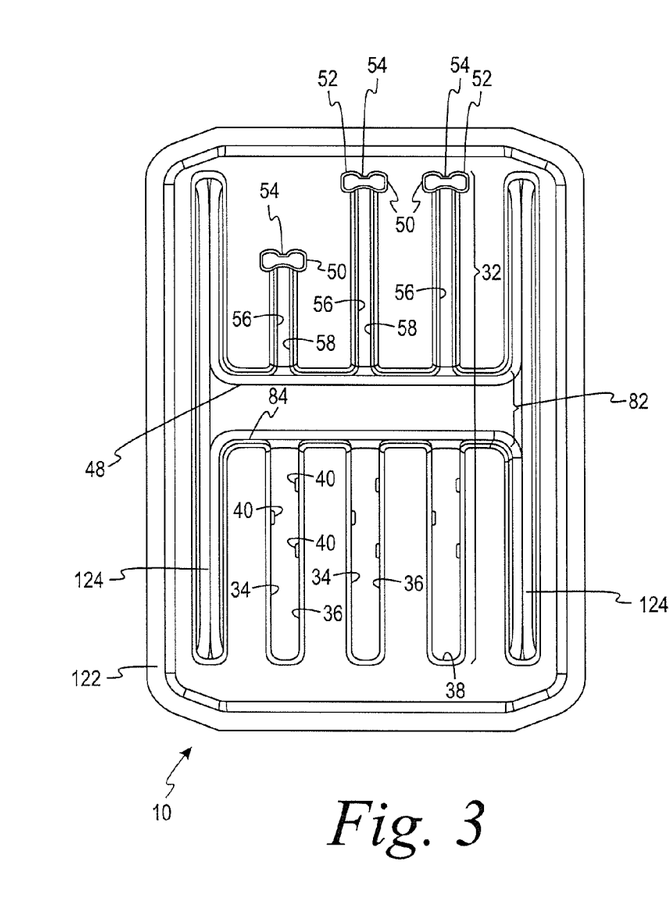
FIG. 3 is a plan view of the syringe storage tray of FIG. 2.
Figure 4:
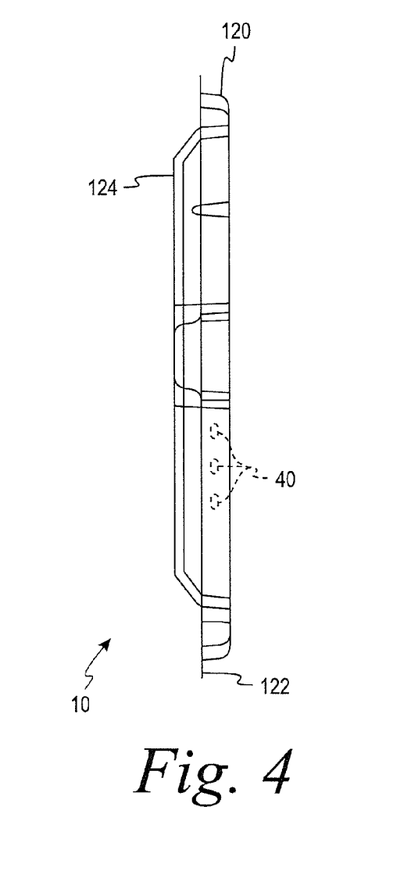
FIG. 4 is a side view of the syringe storage tray of FIG. 2.

As shown in FIG. 1, the storage tray 10 is configured to receive one or more prefilled syringes 12 (with three being shown). As is typical, each illustrated syringe 12 comprises a plunger 14 having a thumb rest 16 on one end of a shaft 18 and a piston or stopper (not seen) on the other end. The piston is received within the bore of a barrel 22, the barrel 22 being formed with opposed finger flanges 24 on one end and a luer lock 28 on the other end. A sheath or cap 30 is received in luer lock 28 and is removed prior to use.

In accordance with the disclosure, and with reference generally to FIGS. 1-4, the tray 10 comprises a recess, generally designated 32, for receipt of each syringe that is to be carried by the tray 10. It is contemplated that a syringe tray as described herein may be used to hold syringes prefilled with a patient's stem cells, the syringes being configured to be connected to a percutaneous transluminal catheter for the transport of the stem cells to the patient's ischemic tissue, for example, cardiac tissue. As illustrated, the tray has three recesses 32, but it could have either more or less depending on, e.g., whether the agent to be administered has multiple components or if multiple doses are to be administered. Thus, a syringe storage tray according to the present disclosure could be configured with one or more recesses 32. Each of the three recesses 12 for the illustrated tray 10 has generally the same configuration. Thus, identical reference numerals will be used to designate structure common to each recess 12.

Each recess 32 preferably comprises three segments: a first segment for holding the syringe barrel 22, a second segment for holding the plunger 14 in a pre-determined axial relation to the barrel, and a third segment intermediate the first and second segments configured to provide access to the portion of the barrel 22 adjacent the finger flanges 24 sufficient to permit the barrel to be gripped by the fingers of a user to remove the syringe from the tray.

Figure 5:
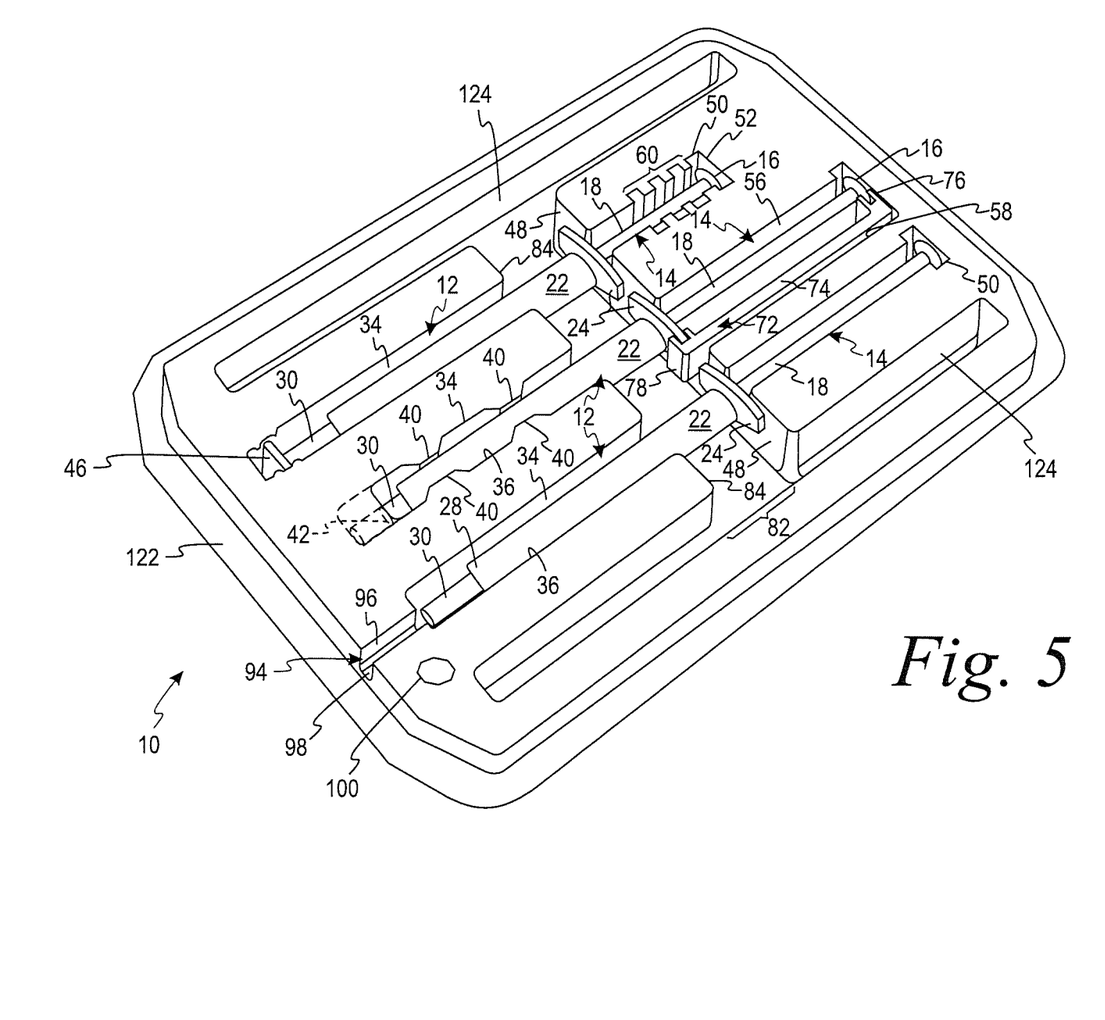
FIGS. 5-7 are perspective views similar to FIG. 1 showing features that may be used in combination with or as an alternative to the various features incorporated into the syringe tray of FIGS. 1-4.

More specifically, the first segment for holding the syringe barrel 22 preferably comprises opposed sidewalls 34, 36 that are spaced to receive the barrel 22 therebetween and an end wall 38. The sidewalls 34, 36 (best seen in FIG. 3) are formed with structures to securely hold the barrel 22 of the syringe 12 in the recess 32, and past which the barrel 22 of the syringe must be forced to remove the syringe 12 from the tray 10. Preferably, the structures are projections or tabs 38 that extend beyond the faces of the sidewalls 34, 36 and into the space therebetween. As illustrated in FIG. 1-4, three tabs 40 are provided, with one tab 40 associated with sidewall 34 and two tabs 40 associated with sidewall 36. However, the number, location and configuration of the tabs 40 may be varied without departing from the scope of the disclosure. For example, as shown in FIG. 5, the sidewalls 34, 36 may be formed with two pairs of opposed elongated tabs 40. Preferably, the tabs 40 have a resilient nature, such that they deform to permit the barrel 22 of the syringe 12 to pass by, and then return to their original configuration. (It should be noted that FIGS. 5-8 illustrate multiple additional features and variations that may or may not necessarily be combined in a single embodiment of a syringe tray as described herein.) If the tray 10 is made from PETE or PETG, as described above, the tabs 40 will inherently possess the required resiliency. Preferably, the tabs provide for a snap fit to securely lock the syringe 12 into the tray 10.

Other structures may be used either in place of or in conjunction with the tabs 38 described above to securely hold and position the syringe barrel 22 in the tray 10. In a first alternative, seen in FIG. 5, the recess 32 may be formed with an aperture 42 in the end wall 38 that is sized to receive the end cap 30 of the syringe. The aperture 42 may have a shape complementary to the cross-sectional shape of the end cap, but smaller than the largest such shape for the end cap, so that the cap 30 is securely held within the aperture 42. The sidewall of the aperture may also be tapered to more securely seat and firmly grip the end cap 30. Thus, when placing a syringe 12 into a tray 10, the end cap 30 is inserted into the aperture 42, and then the barrel 22 is snapped into place between the projections 40.

Alternatively, the tray may be formed with, or be configured to receive, a clip 44 (seen in FIG. 7) that receives the end cap 30 of the syringe 12. The clip 44 is preloaded when inserting a syringe into the tray to apply a torque to the end cap 30 in a direction to screw the end cap into the luer lock 28. Similarly, the end wall 38 can be formed to receive a separately-made biasing member that engages the tip of the syringe and exerts an axial force on the barrel 22. The biasing member may comprise, for example, a spring clip 46 (as illustrated in FIG. 5), a coil spring, a resilient foam, or the like, to exert an axial force on the barrel 22 such that the finger flanges 24 are forced against lateral wall 48 in the tray opposite the end wall 38, thus positively locating the barrel 22 in the tray 10.

The syringe barrel 22 may additionally or alternatively be axially biased toward the end wall 37 by various means on the lateral wall 48 that engage the finger flanges 24. Such means may include projections or tabs integrally formed in the lateral wall 48 during the molding of the tray (similar to the tab 54, described below) or resilient means, such as springs, clips or foam, secured to the lateral wall 48 so as to engage the finger flanges 24.

Other means for securing the barrel 22 in the tray 10 may also be employed. For example, the first recess may be configured to define an aperture sized to receive the barrel of a syringe and further include spring fingers that extend into the aperture to engage the barrel to hold it securely in place, similar to a spring or push nut.

The second segment of the recess 32 is configured to receive the plunger 14 so as to prevent relative movement between the plunger 14 and the barrel 22. Specifically, motion of the plunger relative to the syringe barrel is sufficiently limited to prevent contamination of the syringe and its contents during transport of the prefilled syringes. In one alternative, the second recess preferably comprises a slot 50 for seating the thumb rest 16 of the plunger 14. The slot 50 is oriented generally transverse or perpendicularly to the slot formed by the sidewalls 34, 36, and further includes an end wall 52. The end wall 52 preferably includes a projecting tab or rib 54 that engages the top of the thumb rest 16 to positively locate the plunger 14 in the tray and limit axial movement of the plunger 14 relative to the barrel 22 of the syringe 12. Preferably, the tab 54 is deformable to account for tolerances in the fabrication of the tray 10 and the filling of the syringes. Alternatively, a separate resilient member, such as a spring or foam member (not shown), may be secured to the end wall 52 for engagement with the thumb rest 16. The second segment also preferably includes sidewalls 56, 58 that, as shown, substantially flank the length of the plunger shaft 18 extending out of the barrel 22 of the syringe 12. The sidewalls 56, 58 may optionally be formed with projections or cleats (not shown) that engage the plunger shaft 18 (similar to tabs 40) to more positively position the plunger in the tray.

Figure 6:
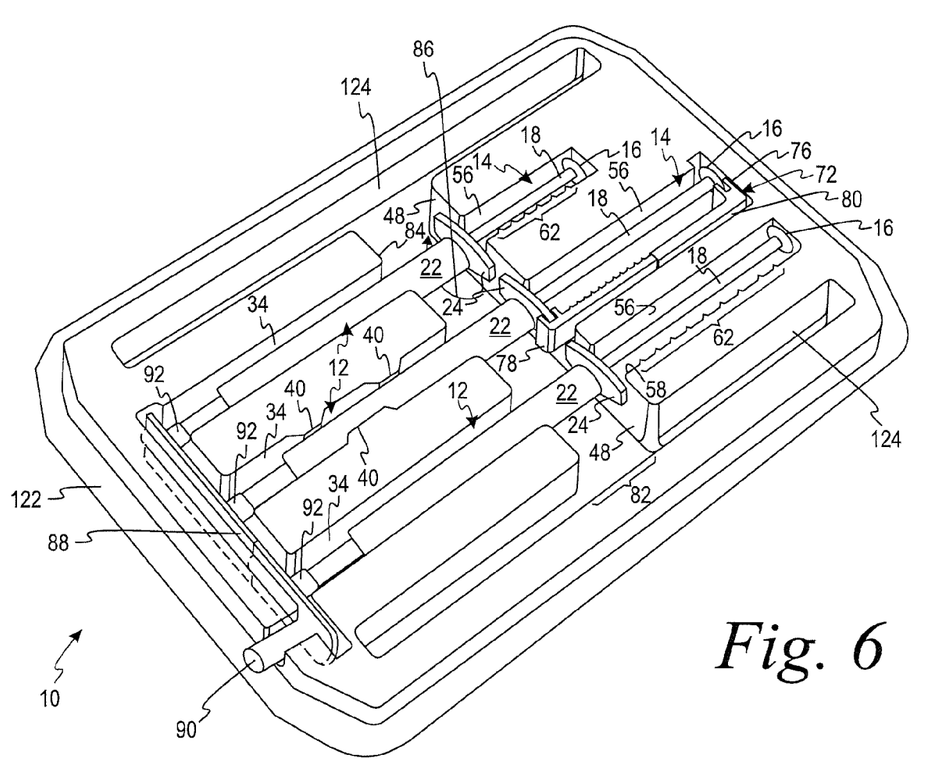

Other means may be utilized for maintaining the position of the plunger 14 relative to the barrel 22. In a first alternative, seen in FIG. 5, the second recess may be formed so as to have a plurality of transversely-oriented spaced slots 60 integrally formed therein configured to receive the thumb rest 16 of the plunger 14. Such a configuration permits the same recess 32 to be used for syringes that are prefilled with different volumes of fluid, and thus have differing positions of the plunger relative to the syringe barrel. In a further alternative, seen in FIG. 6, one or both of the sidewalls 56, 58 may be formed with a series of projecting teeth or detents 62 (as seen in FIG. 6) that engage the thumb rest 16 for various plunger settings, and thus similarly permit the second recess to accommodate syringes having multiple different thumb rest locations.

Figure 7:
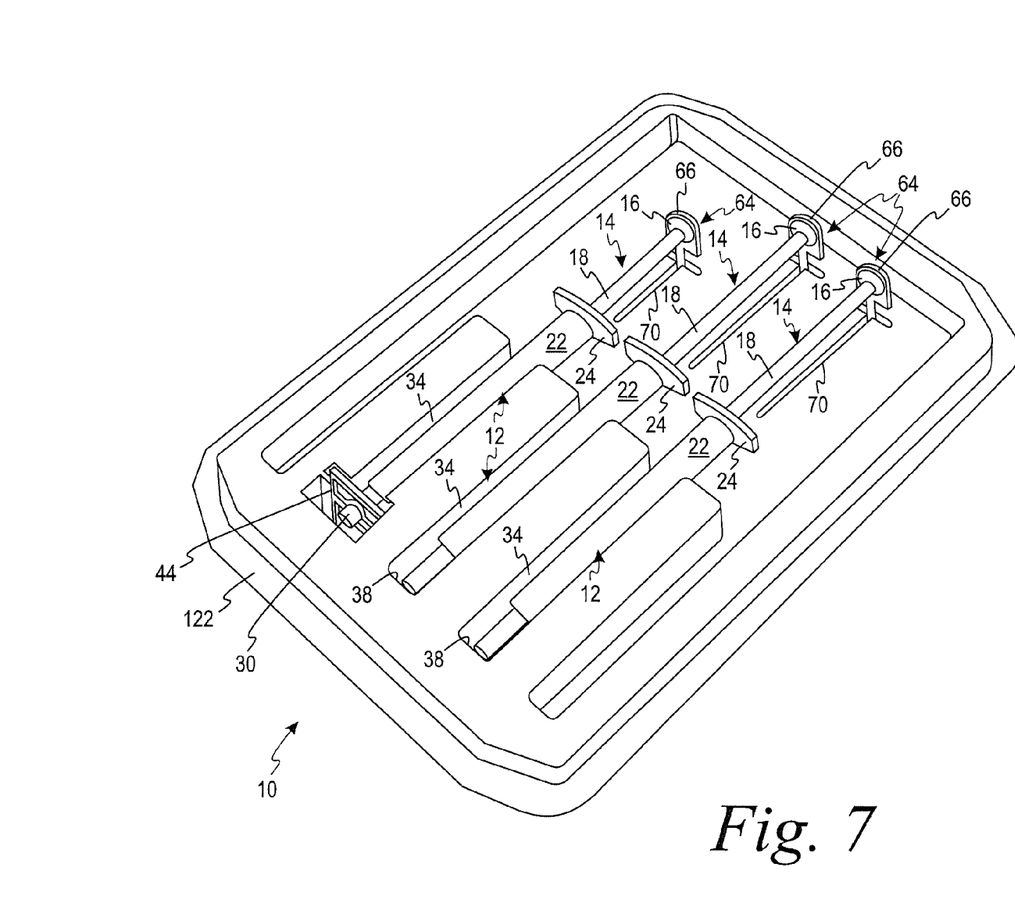
Figure 7A:
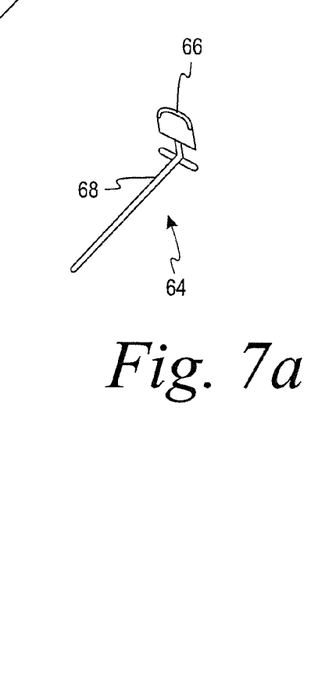
FIG. 7a is a perspective view of a clip that may be used in combination with the embodiment shown in FIG. 7.

The means for securing the thumb rest of the syringe to the tray may also be formed separately from the tray and then secured thereto. For example, as shown in FIG. 7, a clip 64 may be received in the tray that has a pocket-like portion 66 that receives and captures the thumb rest and further comprises a support structure 68 configured to be received in a recess 70 in the tray 10. The support structure 68 may have a cross-like shape that is received in a T-shaped recess 70 to prevent axial and rotational movement and positively locate the clip 64 within the recess 70.

As a further alternative means separate from the tray may be utilized to maintain the relative position of the plunger to the syringe barrel. For example, a spacer bar may be employed that removably attaches to both the barrel and the plunger. More specifically, and as seen in FIG. 5, the spacer bar 72 may comprise an elongated member 74 having a structure 76 on one end that engages or captures the thumb rest 16 of the plunger 14 and a structure 78 on the other end that engages or captures the finger flanges 24 of the barrel 22. Spacers 72 of various sizes may be provided to accommodate syringes having different volumes of fluid therein. Alternatively, and with reference to FIG. 6, the elongated portion of the spacer may comprise a telescoping member 80 that is adjustable in length. The telescoping member 80 preferably includes means for maintaining the desired spacing of the end structures. For example, one of the telescoping members could include a gear rack and the other a cooperating ratchet tooth (similar to a cable tie), although other means may occur to one skilled in the art. If a separate spacer is used, the tray 10 is configured to accommodate the spacer by, for example, increasing the spacing between the sidewalls 56, 58.

The third segment of the tray comprises a relieved portion 82 that provides access to the syringe barrel 22 to facilitate removal of the syringe 12 from the tray 10. As illustrated, the relieved portion 82 is located intermediate the first segment and second segment and is defined by opposed sidewalls 48, 84. However, the third segment could be located within the first segment. As described above and seen in FIG. 1, sidewall 48 is preferably positioned so as to abut the finger flanges 24 of the barrel 22 when a syringe 12 is held in the recess 32, with the tip of the needle sheath 30 either contacting the end wall 38 of the first segment or otherwise being engaged or secured in the tray as described above. As such, the barrel 22 is unable to move axially within the tray 10. Sidewall 84 is spaced from sidewall 48 a distance sufficient to permit finger access to the barrel. Optionally, the relieved portion 82 may have a depth sufficient to permit rotation of the syringe barrel 22 about its longitudinal axis (as shown by the arrow 86 in FIG. 6). To this end, the depth of the relieved portion 82 is preferably greater than the combined width of the finger flanges 24 and diameter of the barrel 22.

In keeping with another aspect of the disclosure, the tray may include additional features that provide greater functionality. For example, as seen in FIG. 6, the tray may be configured to receive a separately made manifold 88 that interconnects in fluid communication each of the syringes 12 to be held in the tray 10. The manifold 88 includes an inlet/outlet port 90 and a series of junction ports 92, one for each syringe, configured so that the barrel 22 of each syringe may be secured to the manifold 88 and to provide fluid communication through the manifold 88 to the interior of the syringe barrel 22. The manifold 88 may be utilized to facilitate the simultaneous filling of the syringes 12 and/or to sequence the use of the syringes 12 during administration of their contents. After filling the syringes 12 by introducing fluid through the inlet/outlet port 90 of the manifold 88, the port of the manifold 88 is sealed by, for example, a separate cap, a self-sealing gasket, or other means as may occur to a person skilled in the art.

Further, the tray may be provided with means that facilitate the removal of the end cap 30 from each syringe 12 which may have been over tightened after filling the syringe 12. Accordingly, the tray 10 may include a structure 94 (as illustrated in FIG. 5) which serves as a wrench for securely holding the end cap. In one alternative, the wrench structure 94 may comprise a slot defined by sidewalls 96, 98. After removing the syringe 12 from the tray, the end cap 30 is wedged between the sidewalls 96, 98. The sidewalls 96, 98 are spaced so that they tightly grip the cap 30, thus permitting the barrel 22 to be twisted relative to the cap 30 to unscrew the cap from the syringe 12. In a second alternative, the syringe tray 10 may be formed with an aperture 100 having a shape complementary to the cross-sectional shape of the end cap 30, but of a size smaller than the largest cross-sectional shape, so that the end cap 30 may be inserted into the aperture 100 to firmly grip the cap 30 and permit its unscrewing from the syringe by the application of torque to the syringe barrel 22.

Figure 8:
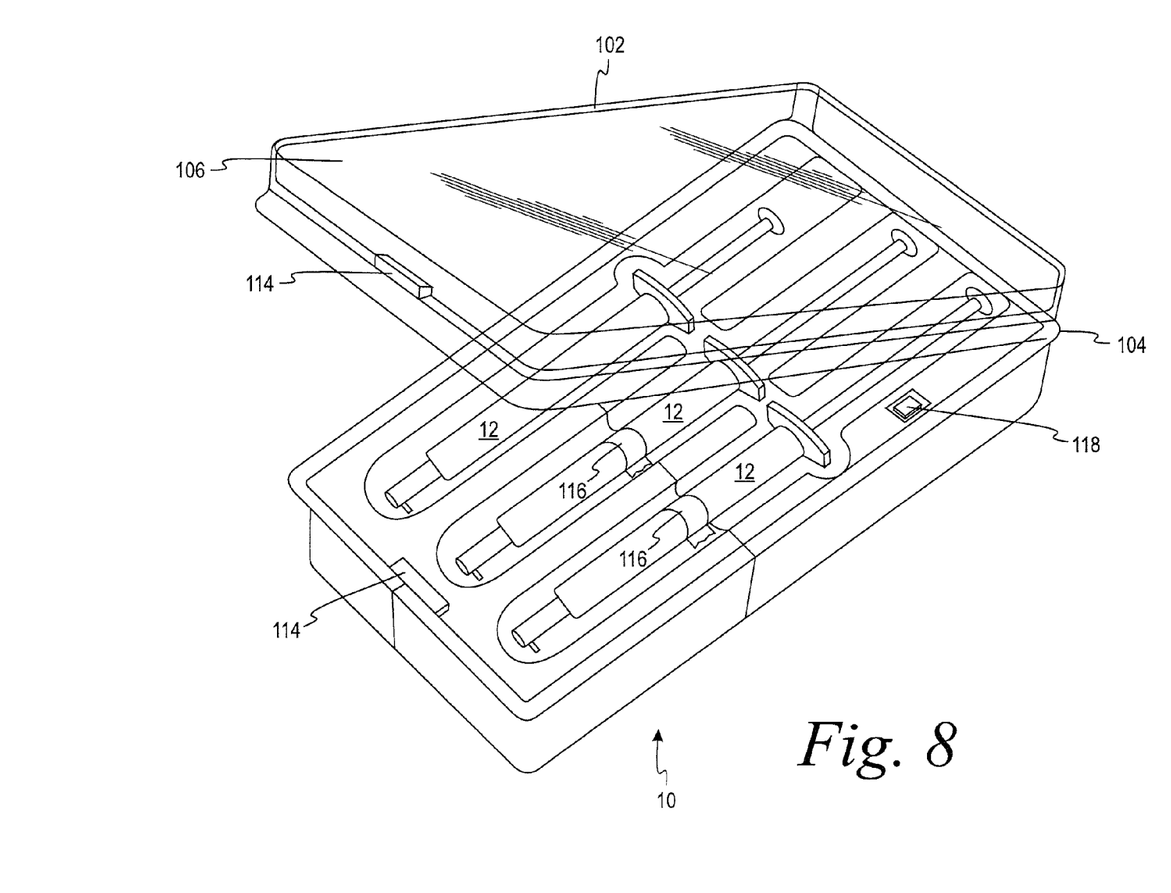
FIGS. 8 and 9 show a syringe tray in combination with further packaging including a cover or closure member.

In keeping with another aspect of the disclosure, the syringe tray 10 may be part of a housing assemblage having a reclosable cover to provide a more durable and protective enclosure for the syringes held in the tray. With reference to FIG. 8, the tray 10 is provided with a cover 102 and is preferably formed integrally with the tray 10, with a living hinge 104, or other hinge structure, connecting the two. The cover 102 preferably has a depth sufficient to receive a resilient/expandable insert or void filler 106, comprising, for example, an encapsulated foam material, that presses against the syringes 12 held in the tray 10 upon closure of the cover 102 to more securely hold the syringes 12 in place and provide additional protection.

The cover 102 and tray 10 are preferably provided with a latch or lock structure 114 (as illustrated in FIG. 8) to secure the cover in the closed position. For example, the latch or lock 114 may comprise a magnet in combination with another magnetic or magnetizable material in opposed relationship on the tray and cover. Alternatively, the cover and tray may be provided with interfitting, complementarily-shaped projections and recesses (not shown) that frictionally engage each other upon closure of the cover 102.

In another aspect of the disclosure, the barrels of the syringes may be provided with a mark indicating the position of the piston within the barrel at the time the filled syringe is secured in the tray. When the syringe tray is unloaded prior to use, the mark provides a visual indication as to whether the piston has moved during shipment. As illustrated in FIG. 8, the barrel marking may comprise a length of tape 116 applied to the barrel, although other means of marking the syringe barrel and/or the tray to indicate the position of the piston may be employed.

Figure 9:
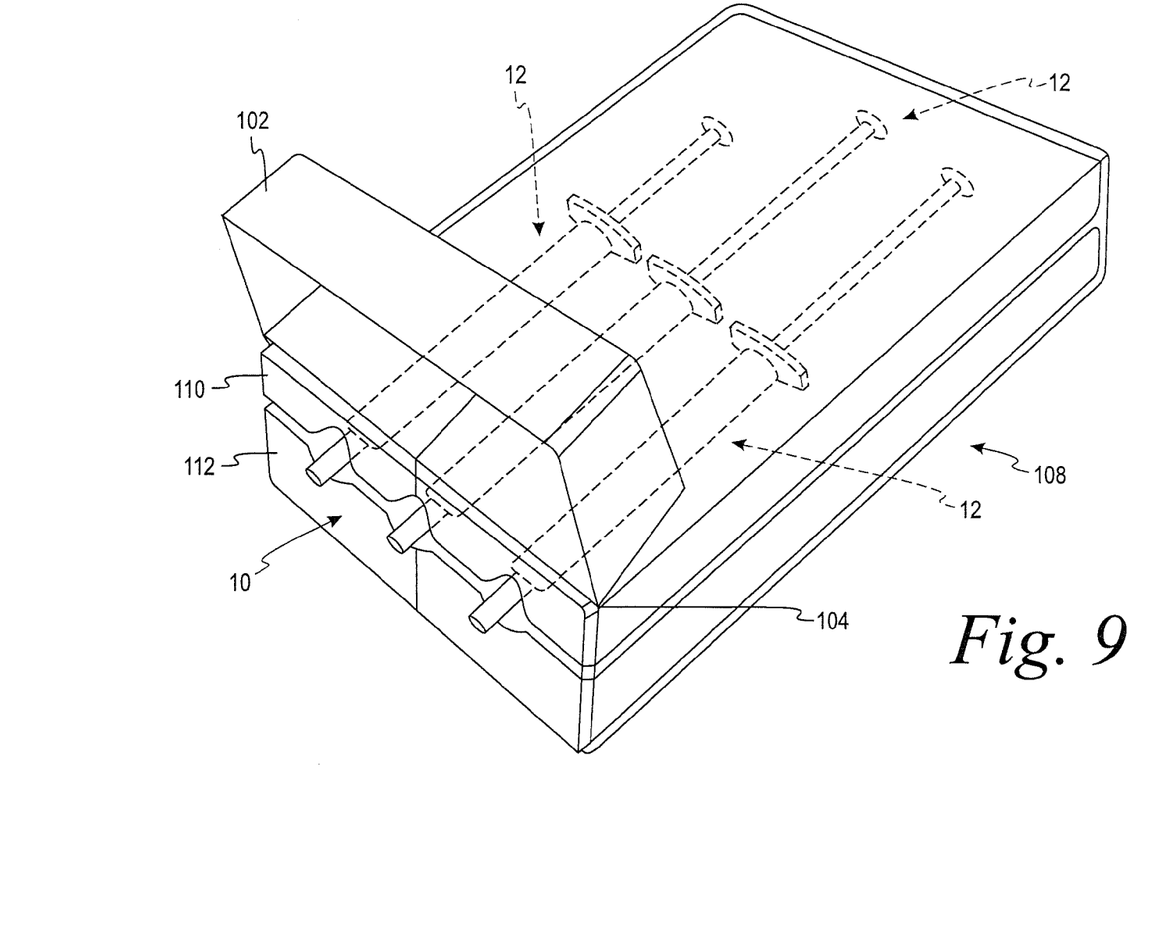

Alternatively, as seen in FIG. 9, a tray 10 loaded with syringes 12 may be received in a separate box-like container 108 open on one end, such that the filled tray 10 is slided into the container 108. As illustrated, the tray comprises deformable members 110, 112, made of a material such as the encapsulated foam described above, for securely positioning the syringes 12 within the container 108, although the container 108 may be configured to receive any of the syringe trays described above. The container 108 is preferably provided with a closure 114 for the open end. In the illustrated embodiment, the closure is hingedly attached to the remainder of the container, although a separate closure that slides over the open end of the container may be used. Preferably, the closure 114 and container 108 include a latch or other means (such as the latches described above) for releasably securing the closure 108 to the container 104 in the closed position to secure the syringe tray 10 therein.

As seen in FIG. 8, the syringe tray may also include a sensor 118 affixed thereto that measures and stores data as to the conditions to which the syringes 12 are subjected during shipment and prior to use that could potentially affect the efficacy of the substances administered by the syringes. Such data could include information as to vibration, temperature, and/or humidity.

The prefilled syringes 12 are preferably placed in tray 10 in an aseptic manner. The combination is then preferably sterilized and a cover is preferably sealed to the tray 10 so as to overlie the syringes. Preferably, the cover may be made of plastic material, such as Tyvek®, that is heat sealed to the top surface of the tray. The tray is then preferably placed in an over-pouch to maintain sterility until the time of use. Double bagging the tray is preferred, with the outer pouch being resealable.

In accordance with another aspect of the disclosure, the tray 10 is configured so as to reduce the likelihood that it could puncture the over-pouch, and thus increase the contamination potential of the syringes. To this end, the tray 10 preferably has no sharp edges, and the corners (such as corners 120) are rounded or beveled. The tray 10 may also be provided with an outer edge in the form of a flange 122 that helps to reduce the angle at which the inner surface of the over-pouch engages the corners 120, thus further reducing the likelihood of puncture. As illustrated, the tray 10 is also formed with a pair of elongated parallel supports 124 that serve to increase the rigidity of the tray and provide a stable base for the tray when placed on a flat surface.

As set forth above, the disclosed device includes the aspects set forth below.

In accordance with one aspect, a storage tray for one or more syringes is provided where each syringe comprises a plunger with a shaft and a thumb rest and a barrel with a proximal end for receipt of the plunger and a tip comprising a distal end. The storage tray comprises a first means for removably securing the barrel of the syringe to the tray and a second means for maintaining a predetermined position of the plunger relative to the barrel.

In accordance with another aspect of the disclosure, one or both of the first means and the second means of the storage tray may be formed integrally with the tray. Alternatively, one or both of the first means and the second means may be formed separately from the tray and then associated therewith.

In accordance with another aspect, which may be used with any one or more of the above aspects, one or both of the first means and the second means may comprise a biasing member.

In accordance with another aspect, which may be used with any one or more of the above aspects, the second means engages the thumb rest of the plunger.

In accordance with a further aspect, which also may be used with any one or more the above aspects, the second means engages the shaft of the plunger.

In accordance with a further aspect, which may be used with any one or more of the above aspects, the first means engages the sidewall of the barrel.

In accordance with a further aspect, which may be used with any one or more of the above aspects, the first means engages the tip of the barrel.

In accordance with another aspect, a storage tray for one or more syringes is provided which comprises a recess for receiving each of the one or more syringes, each recess comprising a first segment configured to hold the barrel of the syringe, and a second segment for holding the plunger, the first segment and second segment configured to retain the barrel and plunger and substantially fixed axial relationship.

In accordance with another aspect, the recess of the storage tray further comprises a third segment configured to provide access to a portion of the barrel that is sufficient to permit gripping of the barrel by the fingers of a user. The third segment may be positioned intermediate the first and second segments or, alternatively, positioned within the first segment.

In accordance with another aspect, which may be used with one or more of the above aspects, the first segment of each recess further comprises first and second opposed sidewalls that define a space therebetween to receive the barrel of the syringe. The first and second sidewalls each have one or more deformable projections thereon protruding into the space between the first and second sidewalls for positively retaining the barrel between the first and second sidewalls. The second segment of each recess further comprises a slot for receiving the thumb rest of the plunger, the slot comprising a third sidewall oriented generally perpendicularly to the first and second sidewalls, and the third sidewall further including a projection for engaging a surface of the thumb rest.

In accordance with a further aspect, which may be used with any one or more of the above aspects, the third segment of each recess further comprises a relieved portion intermediate the first and second sidewalls and the slot.

In accordance with another aspect, which may be used with any one or more of the above aspects, each recess comprises a third and fourth opposed sidewalls for receipt of a length of the plunger disposed between the thumb rest and the proximal end of the barrel.

In accordance with a further aspect, which may be used in combination with any one or more of the above aspects, the storage tray comprises a plurality of corners, the corners being rounded.

In accordance with another aspect, which may be used with any one or more of the above aspects, the storage tray further comprises an outer edge in the form of a flange.

In accordance with another aspect, which may be used with any one or more of the above aspects, each recess is configured to hold a prefilled syringe.

In accordance with another aspect which may be used with any one or more of the above aspects, the storage tray further comprises a pre-filled syringe received in each recess.

Thus, an improved syringe storage tray has been disclosed. The description provided above is intended for illustrative purposes only, and is not intended to limit the scope of the disclosure to any specific embodiment described herein.

The invention claimed is:

1. A storage tray for one or more syringes, each such syringe comprising a plunger with a thumb rest and a barrel having a proximal end for receipt of the plunger, the storage tray comprising:
a recess receiving each of the one or more syringes, each recess comprising a first segment configured to hold the barrel of the syringe, and a second segment for holding the plunger, the first segment and second segment configured to retain the barrel and plunger in substantially fixed axial relationship; and
a spacer bar, independent of the tray, attached to the one or more syringes, disposed in the second segment of the recess, and removably attached to the barrel and the plunger to maintain the relative position of the plunger to the syringe barrel,
wherein the spacer bar prevents the plunger from being both depressed into and extended out of the syringe barrel.

2. The storage tray of claim 1 wherein the recess further comprises:
a third segment configured to provide access to a portion of the barrel sufficient to permit gripping of the barrel by fingers of a user.

3. The storage tray of claim 2 wherein the third segment is positioned intermediate the first and second segments.

4. The storage tray of claim 2 wherein the third segment is positioned within the first segment.

5. The storage tray of claim 1 wherein:
the first segment of each recess further comprises first and second opposed sidewalls defining a space therebetween to receive the barrel of a syringe, the first and second sidewalls each having one or more deformable projections thereon protruding into the space between the first and second sidewalls for positively retaining the barrel between the first and second sidewalls; and
the second segment of each recess further comprises at least one slot for receiving the thumb rest of the plunger, the slot being oriented transverse to the first and second sidewalls, and configured to receive the thumb rest.

6. The storage tray of claim 5 wherein the slot comprises a third sidewall generally transverse to the first and second side walls, the third sidewall including a further projection for engaging a surface of the thumb rest.

7. The storage tray of claim 2 wherein:
the third segment of each recess further comprises a relieved portion intermediate the first and second segment and the relieved portion for providing access to a proximal portion of the barrel to facilitate removal of the syringe from the tray.

8. The storage tray of claim 1 further comprising a plurality of corners, the corners being rounded.

9. The storage tray of claim 1 further comprising an outer edge in the form of a flange.

10. The storage tray of claim 1 further comprising a prefilled syringe received in each recess.

11. The storage tray of claim 1 further comprising each recess having a third and fourth opposed sidewalls for receipt of a length of the plunger disposed between the thumb rest and the proximal end of the barrel.

12. The storage tray of claim 1 wherein each recess is configured to hold a prefilled syringe.

13. A storage tray for one or more syringes, each such syringe comprising a plunger with a shaft and a thumb rest and a barrel having a proximal end for receipt of the plunger and a tip comprising the distal end, the storage tray comprising:
first means for removably securing the barrel of the syringe to the tray;
second means for maintaining a predetermined position of the plunger relative to the barrel; and
a spacer bar disposed in a second segment of a recess in the tray and removably attached to the barrel and the plunger to maintain the relative position of the plunger to the syringe barrel, and removable from the tray,
wherein the spacer bar prevents the plunger from being both depressed into and extended out of the syringe barrel.

14. The storage tray of claim 13 wherein one or both of the first means and the second means is formed integrally with the tray.

15. The storage tray of claim 13 wherein one or both of the first means and the second means comprises a biasing member.

16. The storage tray of claim 13 wherein the second means engages the thumb rest of the plunger.

17. The storage tray of claim 13 wherein the second means engages the shaft of the plunger.

18. The storage tray of claim 13 wherein the first means engages the side wall of the barrel.

19. The syringe tray of claim 13 wherein the first means engages the tip of the barrel.

20. The storage tray of claim 1 wherein the spacer bar is provided to accommodate one or more volumes formed by the barrel and the plunger.

21. The storage tray of claim 13 wherein the spacer bar is provided to accommodate one or more volumes formed by the barrel and the plunger.

* * * * *